United States Patent
Yang et al.

(10) Patent No.: US 8,562,731 B2
(45) Date of Patent: Oct. 22, 2013

(54) FUNGAL MODIFIED CHITOSAN ADHESIVES AND WOOD COMPOSITES MADE FROM THE ADHESIVES

(75) Inventors: Dian-Qing Yang, Quebec (CA); Yaolin Zhang, Quebec (CA); Xiang-Ming Wang, Quebec (CA); Hui Wan, Quebec (CA); Gilles Brunette, Quebec (CA)

(73) Assignee: Fpinnovations, Pointe-Claire, Quebec (CA)

( * ) Notice: Subject to any disclaimer, the term of this patent is extended or adjusted under 35 U.S.C. 154(b) by 320 days.

(21) Appl. No.: 13/011,337

(22) Filed: Jan. 21, 2011

(65) Prior Publication Data

US 2011/0190424 A1    Aug. 4, 2011

Related U.S. Application Data (60) Provisional application No. 61/300,077, filed on Feb. 1, 2010.

(51) Int. Cl.
| | | |
|---|---|---|
| C08L 1/00 | (2006.01) | |
| C08L 3/00 | (2006.01) | |
| C08L 5/00 | (2006.01) | |
| C08G 8/00 | (2006.01) | |
| C08B 30/00 | (2006.01) | |
| C09D 101/00 | (2006.01) | |
| C09D 103/00 | (2006.01) | |
| C09D 105/00 | (2006.01) | |
| C09J 101/00 | (2006.01) | |
| C09J 103/00 | (2006.01) | |
| C09J 105/00 | (2006.01) | |

(52) U.S. Cl.
USPC ............ 106/162.1; 127/34; 527/303

(58) Field of Classification Search
USPC ............ 127/34; 106/162.1; 527/303
See application file for complete search history.

(56) References Cited

U.S. PATENT DOCUMENTS

4,806,474 A * 2/1989 Hershberger ............ 435/101
4,970,150 A * 11/1990 Yaku et al. ............ 435/101

(Continued)

FOREIGN PATENT DOCUMENTS

| CA | 2722443 | 2/2001 |
|---|---|---|
| CN | 101402833 A | 4/2008 |

(Continued)

OTHER PUBLICATIONS

Peshkova S. et al., "Investigation of Chitosan-Phenolics Systems as Woo Adhesives", J. Biotechnol., Apr. 24, 2003, vol. 102(2), p. 199-207 (ISSN 0168-1656).

(Continued)

*Primary Examiner* — Liam Heincer
(74) *Attorney, Agent, or Firm* — Norton Rose Fulbright Canada LLP (57) ABSTRACT

The present invention describes a fungal modified chitosan adhesive for binding a fibrous material and the method of producing the adhesive. The adhesive is produced by providing a chitosan containing raw material; a fungal growing medium; a fungal culture; mixing the raw material, the growing medium and the fungal culture together to produce a suspension; incubating the suspension to produce a broth comprising a modified chitosan solid, an at least partially-consumed medium liquid and a fungal residue; separating the modified chitosan solid from the liquid and the fungal residue, and dissolving the modified chitosan solid to produce the adhesive resin.

20 Claims, 4 Drawing Sheets

(56) References Cited

U.S. PATENT DOCUMENTS

| | | | |
|---|---|---|---|
| 5,232,842 A * | 8/1993 | Park et al. | 435/101 |
| 5,290,687 A * | 3/1994 | Suslow et al. | 435/69.1 |
| 5,482,843 A * | 1/1996 | Brzezinski | 435/84 |
| 6,004,795 A * | 12/1999 | Thireos et al. | 435/227 |
| 6,090,928 A | 7/2000 | Donges et al. | 536/20 |
| 6,407,040 B1 * | 6/2002 | Nichols | 504/140 |
| 6,437,107 B1 * | 8/2002 | Tokuyasu et al. | 536/20 |
| 6,485,946 B1 * | 11/2002 | Chen et al. | 435/101 |
| 6,890,913 B2 * | 5/2005 | Chan et al. | 514/55 |
| 7,052,722 B2 * | 5/2006 | Son et al. | 424/725 |
| 7,189,326 B2 * | 3/2007 | Domard et al. | 210/679 |
| 7,288,532 B1 * | 10/2007 | Payne et al. | 514/55 |
| 7,384,772 B2 * | 6/2008 | Howard et al. | 435/200 |
| 7,413,881 B2 * | 8/2008 | Fan et al. | 435/101 |
| 7,488,812 B2 * | 2/2009 | Trinkle et al. | 536/20 |
| 7,998,723 B2 * | 8/2011 | Mori et al. | 435/256.7 |
| 2004/0121442 A1 * | 6/2004 | Chet et al. | 435/200 |
| 2004/0167323 A1 * | 8/2004 | Chan et al. | 536/20 |
| 2005/0019873 A1 * | 1/2005 | Struszczyk et al. | 435/84 |
| 2005/0112750 A1 * | 5/2005 | Howard et al. | 435/200 |
| 2005/0130273 A1 * | 6/2005 | Versali et al. | 435/85 |
| 2005/0215774 A1 * | 9/2005 | Trinkle et al. | 536/20 |
| 2007/0087997 A1 * | 4/2007 | Struszczyk et al. | 514/55 |
| 2007/0129326 A1 * | 6/2007 | Struszczyk et al. | 514/55 |
| 2007/0218046 A1 * | 9/2007 | Vaaje-Kolstad et al. | 424/94.61 |
| 2010/0159557 A1 * | 6/2010 | Liu et al. | 435/174 |
| 2010/0310633 A1 * | 12/2010 | Moerschbacher et al. | 424/445 |

FOREIGN PATENT DOCUMENTS

| | | | |
|---|---|---|---|
| CN | 101575623 A | * | 11/2009 |
| JP | 2003221571 A | | 8/2003 |
| JP | 2005081815 A | | 3/2005 |

OTHER PUBLICATIONS

Dutkiewicz J., "Preparation of Cured Urea-Formaldehyde Resins of Low Formaldehyde Emission", J. Appl. Polym. Sci., Jan. 1984, vol. 29(1), p. 45-55.

Stoilova O. et al., Hydrolysis of Chitosan, Chitosan-Polyoxyethylene and Chitosan-Poly(2-Acryloylamido-2-Methylpropanesulfonic Acid) by a Crude Enzyme Complex from Trichoderma viride, J. Bioact. Compat. Polym., Sep. 2001, vol. 16(5), p. 379-392 (ISSN 0883-9115).

* cited by examiner

FIG. 4

FUNGAL MODIFIED CHITOSAN ADHESIVES AND WOOD COMPOSITES MADE FROM THE ADHESIVES

CROSS-REFERENCE TO RELATED APPLICATION

This application claims the benefit under 35 USC §119(e) of U.S. Provisional Application Ser. No. 61/300,077, filed Feb. 1, 2010.

FIELD OF THE INVENTION

The present invention relates to adhesives made with fungal modified chitosan and the wood composites that are made from the adhesives.

BACKGROUND ART

There is growing demand for formaldehyde free and formaldehyde reduced resins for the manufacturing of composite wood and/or paper products used in buildings. These composite products are structural or non-structural panels commonly used in constructing wall, floor, roof, doors, cabinets, furniture, and architectural mouldings. The main currently used wood adhesives are formaldehyde-based resins, such as urea-formaldehyde (UF), phenol-formaldehyde (PF) and melamine-formaldehyde (MF) resins, and the composite products made of these resins are most common plywood, oriented strandboard (OSB), particleboard (PB) or medium density fiberboard (MDF) that may have various overlays and finishes.

Formaldehyde vapour is hazardous to human health; some programs such as LEED (Leadership in Energy and Environmental Design) and Greenguard allow manufacturers to earn credits for producing non-formaldehyde or low formaldehyde resin products. Such programs are becoming important elements of the marketing strategy of most manufacturers of composite products, cabinets and furniture. Consumers are increasingly asking suppliers of OSB, PB, MDF and plywood to produce formaldehyde free or low-formaldehyde containing products.

Some examples of such aldehyde free or reduced resins are known. JP2003-221571 by Umemura describes a wood adhesive composition comprising tannic acid and chitosan as essential components for wood. An acid is used to dissolve the chitosan to produce an adhesive which can be used for various types of wood products including plywood and particleboard.

JP2005-081815 by Hiromatsu discloses a plywood panel that reduce formaldehyde emissions by suppressing the amount of formaldehyde emitted from the plywood panel by using an adhesive containing chitosan that behaves as an adsorbent of formaldehyde from the heat curable resin.

Peshkova, A. et al. in *Investigation of chitosan-phenolics systems as wood adhesives* (Journal of Biotechnology 102: 199-207, 2003) describe chitosan-phenolic systems as wood adhesives. Peshkova et al. describe that adhesive strengths of the resins tested were directly related to the viscosity of the adhesive systems and afforded lap shear strengths less than 270 psi (approximately 1862 kPa).

Although available there is still a great need for resins produced with low-formaldehyde or free of formaldehyde that have excellent performance and low cost. Developing novel types of adhesives for green composite panel production from renewable natural resource, and reducing environmental impact of VOC emissions from composite products are strategically important for next generation green building.

Chitosan is an amino polysaccharide deacetylated from chitin, which is naturally occurring in large amount in shells of marine crustaceans such as crabs and shrimps and in cell wall of fungi. The chemical structure of chitosan consists of $\beta$-1,4-linked D-glucosamine residues with a number of randomly located N-acetyl-glucosamine. Chitosan is soluble in weakly acidic aqueous solutions and presents in a cationic polyelectrolyte form, which creates the possibility for interactions with negatively charged molecules. In other words, chitosan possesses an adhesive property. Chitosan has received much attention as a potential polysaccharide resource in various fields, and it has been studied extensively for medical and industrial applications.

SUMMARY

It is therefore an aim of the present invention to provide an adhesive resin that is free of or that has lower levels of formaldehyde, while retaining excellent binding properties for fibrous materials.

Therefore, in accordance with one aspect of the present invention, there is provided a fungal modified chitosan adhesive for binding a fibrous material produced by providing a chitosan containing raw material; providing a fungal growing medium; providing a fungal culture; mixing the raw material, the growing medium and the fungal culture together to produce a suspension; incubating the suspension to produce a broth comprising a modified chitosan solid, an at least partially-consumed medium liquid and a fungal residue; separating the modified chitosan solid from the liquid and the fungal residue, and dissolving the modified chitosan solid to produce the adhesive resin.

In accordance with one aspect of the present invention, there is provided the adhesive described herein, wherein dissolving the modified chitosan is in an acid.

In accordance with another aspect of the present invention, there is provided the adhesive described herein, wherein dissolving the modified chitosan is in at least one of a urea formaldehyde resin or a phenol formaldehyde resin.

In accordance with yet another aspect of the present invention, there is provided the adhesive described herein, wherein the dissolving is combined with: an in situ polymerization of a phenolic resin with the modified chitosan, or an in situ polymerization of a urea formaldehyde (UF) resin with the modified chitosan.

Therefore, in accordance with another aspect of the present invention, there is provided method of producing an adhesive resin for binding fibrous products comprising providing a chitosan containing raw material; providing a fungal growing medium; providing a fungal culture; mixing the raw material, the growing medium and the fungal culture together to produce a suspension; incubating the suspension to produce a broth comprising a modified chitosan solid, an at least partially-consumed medium liquid and a fungal residue; separating the modified chitosan solid from the liquid and the fungal residue, and dissolving the modified chitosan solid to produce the adhesive resin.

In accordance with still another aspect of the present invention, there is provided the method described herein, wherein dissolving the modified chitosan solid is in an acid.

In accordance with yet still another aspect of the present invention, there is provided the method described herein, wherein dissolving the modified chitosan solid is in at least one of a urea formaldehyde resin or a phenol formaldehyde resin.

In accordance with a further aspect of the present invention, there is provided the method described herein, wherein the dissolving is combined with: an in situ polymerization of a phenolic resin with the modified chitosan, or an in situ polymerization of a urea formaldehyde (UF) resin with the modified chitosan.

BRIEF DESCRIPTION OF THE DRAWINGS

Reference will now be made to the accompanying drawings, showing by way of illustration a particular embodiment of the present invention and in which.

DETAILED DESCRIPTION OF PARTICULAR EMBODIMENTS

Figure 1:
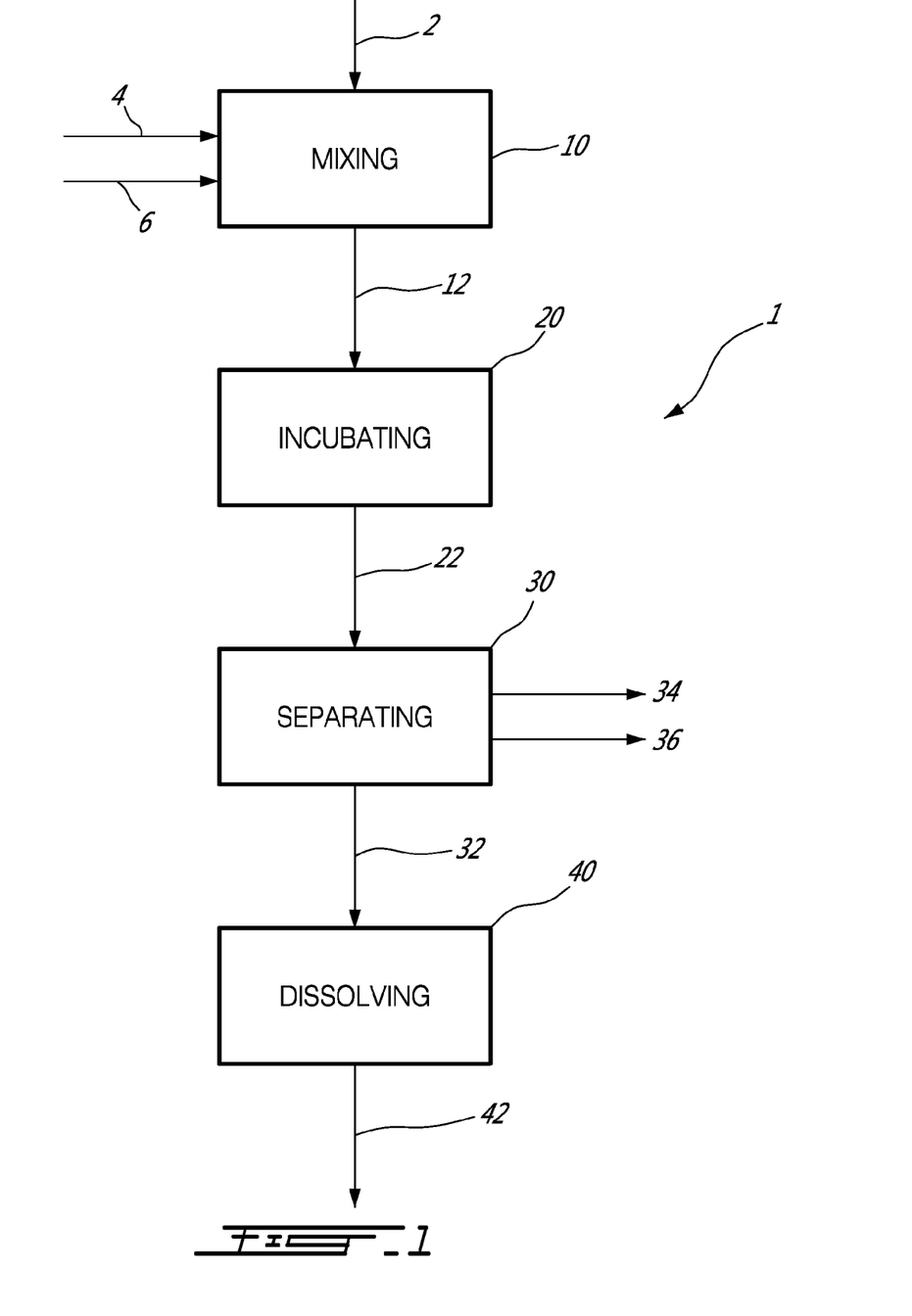
FIG. 1 is a block diagram of a method for producing an adhesive resin for binding fibrous materials according to one embodiment of the present invention.

Referring now to the drawings, where FIG. 1 illustrates a block diagram of a method (1) for producing an adhesive resin for binding fibrous materials. Fibrous materials are understood to comprise various cellulosic materials that include but are not limited to: paper, wood, plywood, strandboard, particleboard, fibreboard and combinations thereof.

The method (1) for producing an adhesive resin starts with providing at least three raw materials: a) a chitosan containing raw material (2); b) a fungal growing medium (4) and c) a fungal culture (6).

In a preferred embodiment the chitosan containing raw material (2) derives from a marine source such as shrimp or crustacean shells.

In a preferred embodiment the fungal growing medium (4) is produced from a sterile aqueous solution of at least one of $KNO_3$, $KH_2PO_4$, $MgSO_4.7H_2O$, $FeCl_3.6H_2O$, polyvinylpyrrolidone, and a nutrient solution containing at least one of a mineral and a vitamin for fungal growth.

In a preferred embodiment the fungal culture is provided in a form of a Mycelia plug (5 mm in diameter) cultured on 2% malt extract agar medium in a Petri dish at 25° C. for one week, it is understood that both the medium and the culture time can be varied. In a preferred embodiment of the fungal cultures are prepared with at least one of the following fungi but are not limited to: *Trichoderma harzianum* Rifai, *Trichoderma viride* Pers.:Fr., and *Gliocladium roseum* Bainier. Other fungal species of Ascomycota or mitosporic fungi may also be used for this purpose.

The three raw materials a), b) and c) listed above are combined or mixed (10) to produce a mixture or suspension (12). The skilled practitioner would understand that more than one Mycelia plug may be used, in a preferred embodiment between three (3) and eight (8) plugs are placed in a suspension (12) of 500 milliliter total volume. In a particularly preferred embodiment five (5) Mycelia plugs (5 mm in diameter) are used in 500 milliliter total volume of suspension (12).

The suspension (12) is either prepared in or carefully transferred to a sterile closed container where it is allowed to incubate. In a preferred embodiment the incubation period for the suspension (12) is for 21 days at 25° C. During this incubation (20), an incubation broth (22) is produced where the fungi in the fungal culture (6) convert the chitosan (2) into a modified chitosan solid (32), while depleting or partially consuming the fungal growing medium (4) thus producing an at least partially consumed medium liquid (34), as well as a fungal residue (36).

The broth (22) is separated (30) by filtering the broth (22) to remove the fungal residue (36), and thus producing a second broth having the modified chitosan solid (32) and the partial consumed medium liquid (34), and then further filtering the second broth to remove the liquid (34) and produce the modified chitosan solid (32), albeit in a humid form of a filter cake. The separation (30) can further include washing the modified chitosan solid (32) with water; drying the modified chitosan solid. The drying in a preferred embodiment is conducted at 50° C. for 3 days and blending or reducing the size of the modified chitosan solid into a fine chitosan powder.

Finally, the fungal modified chitosan solid preferably in a dried powder form or less preferred as a humid filter cake must be dissolved (40) to produce the adhesive resin (42) in liquid form. The preferred means of dissolving the fungal modified chitosan solid is using an acid, wherein a preferred embodiment dilute acetic acid (1 wt % acetic acid) may be used. However, other acids including formic acid; lactic acid; hydrochloric acid; nitric acid and sulphuric acid alone or in combination may also be used for this dissolution.

In a preferred embodiment the dissolution of the fungal modified chitosan solid is in at least one of a urea formaldehyde resin or a phenol formaldehyde resin.

It has surprisingly been found that the fungal modified chitosan solid of the present invention has excellent adhesive properties for fibrous materials. The adhesive properties of the modified chitosan resins are superior to that of non-modified chitosan resins, while eliminating formaldehyde emissions from fibrous board made with such adhesives when compounded without formaldehyde resins, and may reduce formaldehyde emissions from fibrous board made with such adhesives even when compounded with formaldehyde containing resins. The nature of these fungal modified chitosan solids is such that they are difficult if not impossible to characterize therefore herein they are defined in terms of the method used to produce them. That is further illustrated by the following examples.

EXAMPLE 1

Preparation of Fungal Modified Chitosan

The chitosan used in this test was obtained from Marinard Biotech of Riviére-au-Renard, Quebec, a marine source. The characteristics of this product are shown in Table 1.

TABLE 1

Characteristics of chitosan used in the test

| Parameters | Characteristics |
|---|---|
| Appearance | Off-white |
| Form | Flake |

TABLE 1-continued

Characteristics of chitosan used in the test

| Parameters | Characteristics |
|---|---|
| Moisture | 5.6% |
| Ash | 0.197% |
| Protein | <0.2% |
| Insoluble matter | <1% |
| Degree of deacetylation | 86.6% |
| Toxic heavy metals (As, Cd, Hg, Pb) | <5 ppm |
| Viscosity (1% wt in 1% acetic acid) | 307 cps |
| Microbial contamination | 890 CFU/g |

Six fungal isolates from 3 fungal species were selected to modify chitosan; they were *Trichoderma harzianum* Rifai (samples: FTK160D, FTK160F), *Trichoderma viride* Pers.: Fr. (samples: FTK161D, FTK161AA), and *Gliocladium roseum* Bainier (samples: FTK321I, FTK321U). All these fungal isolates came from the Culture Collection of Wood-inhabiting Fungi of FPInnovations, Quebec, Canada. The cultures were maintained in a liquid nitrogen reservoir for cryopreservation at −198° C. before use.

The fungal cultures were first grown on a 2 wt % malt extract agar medium in Petri plates at 25° C. for one week. Mycelia plugs (5 mm in diameter) were cut from each fungal colony and transferred 5 plugs to 1 L flasks, each containing 500 mL of a specific sterile medium consisting 10 g of $KNO_3$, 5 g of $KH_2PO_4$, 2.5 g of $MgSO_4.7H_2O$, 3.3 mg of $FeCl_3.6H_2O$, 20 g of chitosan, 10 g polyvinylpyrrolidone, 150 mL of a nutrient solution containing at least one mineral and/or one vitamin for fungal growth (for example V8 juice), and finally adjusted with distilled water to 1 L. The pH of the medium was 6.0. The flasks were cultured on a shaker (125/rpm) at 25° C. for 21 days. After incubation, the fungal cultures were first filtered through a layer of cheese cloth to remove mycelia plugs and fungal residue, and then filtered through No. 1 filter to remove medium liquid. The slurry of chitosan was washed with sterile distilled water and filtered twice to get rid of any remained medium. The final slurry of chitosan was dried at 50° C. for 3 days to dryness and blended into powder for ready to use. The color of modified chitosan changed with fungal species used. The chitosan modified by *Gliocladium roseum* was yellowish, whereas that modified by *Trichoderma harzianum* was light brownish, and that modified by *Trichoderma viride* was brownish.

EXAMPLE 2

Preparation of Adhesive Resins with Fungal Modified Chitosan

Three types of adhesives were prepared with fungal modified chitosan, i.e. adhesives made of fungal modified chitosan alone, reinforced phenol-formaldehyde (PF) resins with fungal modified chitosan, and reinforced urea-formaldehyde (UF) resins with fungal modified chitosan. The resins made of fungal modified chitosan alone were prepared with the following procedure. Each fungal modified chitosan powder was weighed 3 grams and added to 100 mL of a solution containing 1 w % acetic acid. The reaction mixture was stirred under room temperature for 1 hour until all chitosan powder was solved (pH 4.75). The second set of resins was made by mixing with a commercial PF resin (GP 5778 Phenolic plywood resin from Georgia-Pacific Chemicals LLC, non-volatile content around 57% w/w, pH around 11.3), 10 wt % of each fungal modified chitosan powder was slowly added into the resin and stirred under room temperature until all chitosan powder was well dispersed. The third set of resins was made of principally mixing with a commercial UF resin (T54 PB 199 UF resin from Hexion, non-volatile content around 60% w/w), 5 wt % of each fungal modified chitosan powder was added into the resin and dispersed in a same way as those of PF resins. A control set of resins made of unmodified chitosan was prepared in the same way as those prepared with fungal modified chitosan. The prepared resins were stored at room temperature for a week until used in composite manufacturing.

Chitosan-phenolic resin may be prepared via in-situ polymerization of phenolic resin with chitosan. The procedure is outlined here: 1) dissolve unmodified or modified chitosan in an acidic condition in a concentration of 1-3 wt %; 2) load the required quantity of phenol in the reactor, followed by 1-30 wt % of the chitosan solution/or dispersion based on chitosan solid to phenol; 3) load the para-formaldehyde or formaldehyde solution in which molar ratio of formaldehyde to phenol is in the range of 2.0 to 3.0 and water to reach a solid content, usually 45-55 wt % depending on the application, such as for plywood or OSB wood composites; and raise temperature to 75° C. or lower; 4) adjust pH to about 8-9 with sodium hydroxide or other alkali solution, and keep the temperature lower than 75° C. for a period of 60-180 minutes to check the free formaldehyde content in the system to make sure the free formaldehyde is lower than 2 wt %; 5) raise the temperature to about 90° C., adjust pH to 10-12 with the alkali or sodium hydroxide solution and check the viscosity (100-1000 cps (centipoises)); and 6) when the viscosity approaches the target value, lower the temperature to 75-80° C., and terminate the reaction when the target viscosity is reached.

Chitosan-UF resin may also be prepared via in-situ polymerization of UF resin with chitosan. The general procedure is outlined here: 1) dissolve unmodified or modified chitosan in an acidic condition in a concentration of 1-3 wt %; 2) load the para-formaldehyde or formaldehyde solution, in which the molar ratio of formaldehyde to urea is in the range of 1-4 and water in a reactor and heat the mix to 65° C.; 3) load 1-30 wt % chitosan solution in the reactor based on chitosan solid to urea solid; 4) load the caustic solution to adjust the pH of the mix to 8.5-9.5; 5) heat the mix to 95° C.; 6) add formic acid to adjust pH to 4-5 and hold temperature till the resin reaches the desired viscosity (100-250 cps); 7) lower the temperature to 75-80° C. and add sodium hydroxide solution to adjust pH to 9-9.5; 8) hold the resin at 75-80° C. for 30-35 min and then cool to 65-70° C.; 9) dehydrate the resin under vacuum to obtain the concentrated resin (60%-65% concentration); and 10) cool the resin to room temperature.

EXAMPLE 3

Preparation and Testing Wood Composites

Yellow birch veneer strips (1.5 mm thick×120 mm wide× 240 mm long) were sliced from fresh yellow birch logs with the long direction being parallel to the wood grains. All veneer strips were conditioned at 20% relative humidity (RH) and 21° C. to reach equilibrium moisture content (EMC) prior to use. Resins prepared above were applied to two surfaces of a core veneer at an amount of 5-6 g resin per 300 $cm^2$ based on standard of plywood testing procedure (CSA Standard O112.0-M1977, 3.2.1. Plywood Shear Test). Three pieces of veneer strips were stacked together after a proper open assembly time and hot-pressed at 140° C. for 15 minutes. The applied pressure to veneer strips was 1500 kPa. After manufacturing, the panels were conditioned at 21° C. and 20% RH (relative humidity) until EMC (equilibrium moisture content)

reached. These three-veneer plywood samples were then cut into testing specimen size (25 mm wide×80 mm long) for lap-shear test.

The lap-shear strengths of these samples were determined by a MTS Alliance RT/50 testing machine with a crosshead speed of 1 mm per minute according to the CSA Standard method O112.0, in a dry and a wet condition. The wet condition specimens were soaked in tap water for 48 hours at room temperature, and then tested according to the same lap-shear method. Sixteen specimens cut from 2 plywood samples were tested for each resin system, and the shear strength of plywood samples made with each resin system was obtain from an average of the 16 specimens tested.

Figure 2:
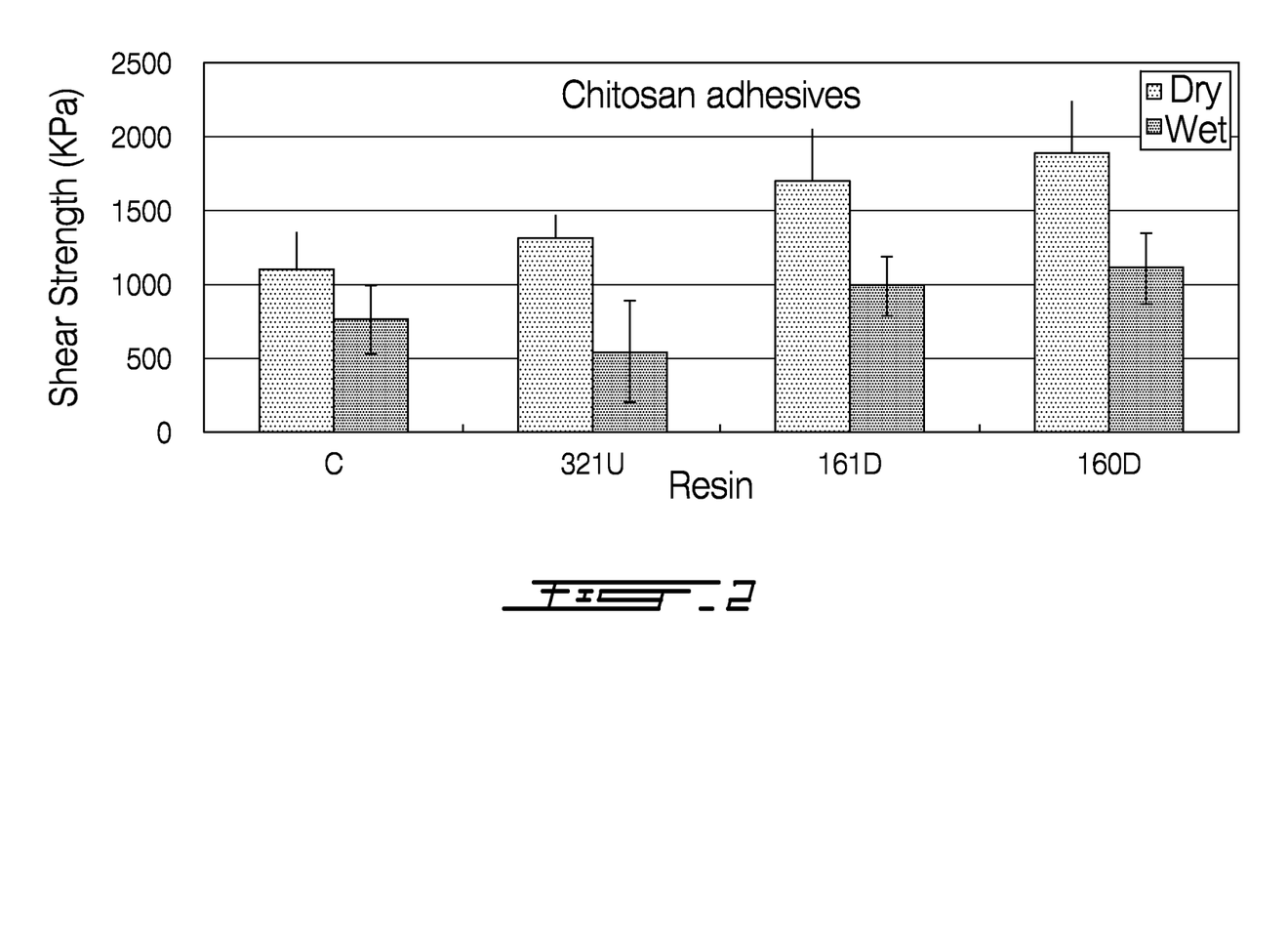
FIG. 2 is a histogram representing shear strengths of plywood samples under wet and dry test conditions comparing adhesives prepared with non-modified chitosan and adhesives using chitosan modified according to several embodiments of the present invention.

The lap-shear strengths of plywood samples made of adhesives of fungal modified chitosan and unmodified chitosan are shown in FIG. 2. The abbreviations below the abscissa in FIG. 2 represent: C=adhesive made of unmodified chitosan; 321U=adhesive made of modified chitosan by fungal species *Gliocladium roseum* (sample: FTK 321U); 161D=adhesive made of modified chitosan by fungal species *Trichoderma viride* (sample: FTK161D); 160D=adhesive made of modified chitosan by fungal species *Trichoderma harzianum* (sample: FTK160D). Furthermore, the term "Dry"=wood composite specimens tested at dry condition; wet=wood composite specimens tested after water soaking for 48 hours. Data are averages of 8 specimens for fungal modified chitosan adhesives and 16 specimens for unmodified control chitosan adhesive.

In the dry test condition, the plywood samples made of unmodified chitosan adhesive had a lap-shear strength of 1100 kPa. The shear strengths of samples made of fungal modified chitosan adhesives were significantly highly. The resin modified chitosan by *Gliocladium roseum* (sample: FTK 321U) was 1318 kPa, which made of modified chitosan by *Trichoderma viride* (sample: FTK161D) was 1698 kPa, and which made of modified chitosan by *Trichoderma harzianum* (sample: FTK160D) was 1892 kPa. At wet test conditions, the shear strengths of panels made of all kind of adhesives were reduced generally compared with the tests at the dry condition. In the wet test, plywood samples made of modified chitosan by *Trichoderma harzianum* (sample: FTK160D) had the superior bonding properties to other adhesives.

Figure 3:
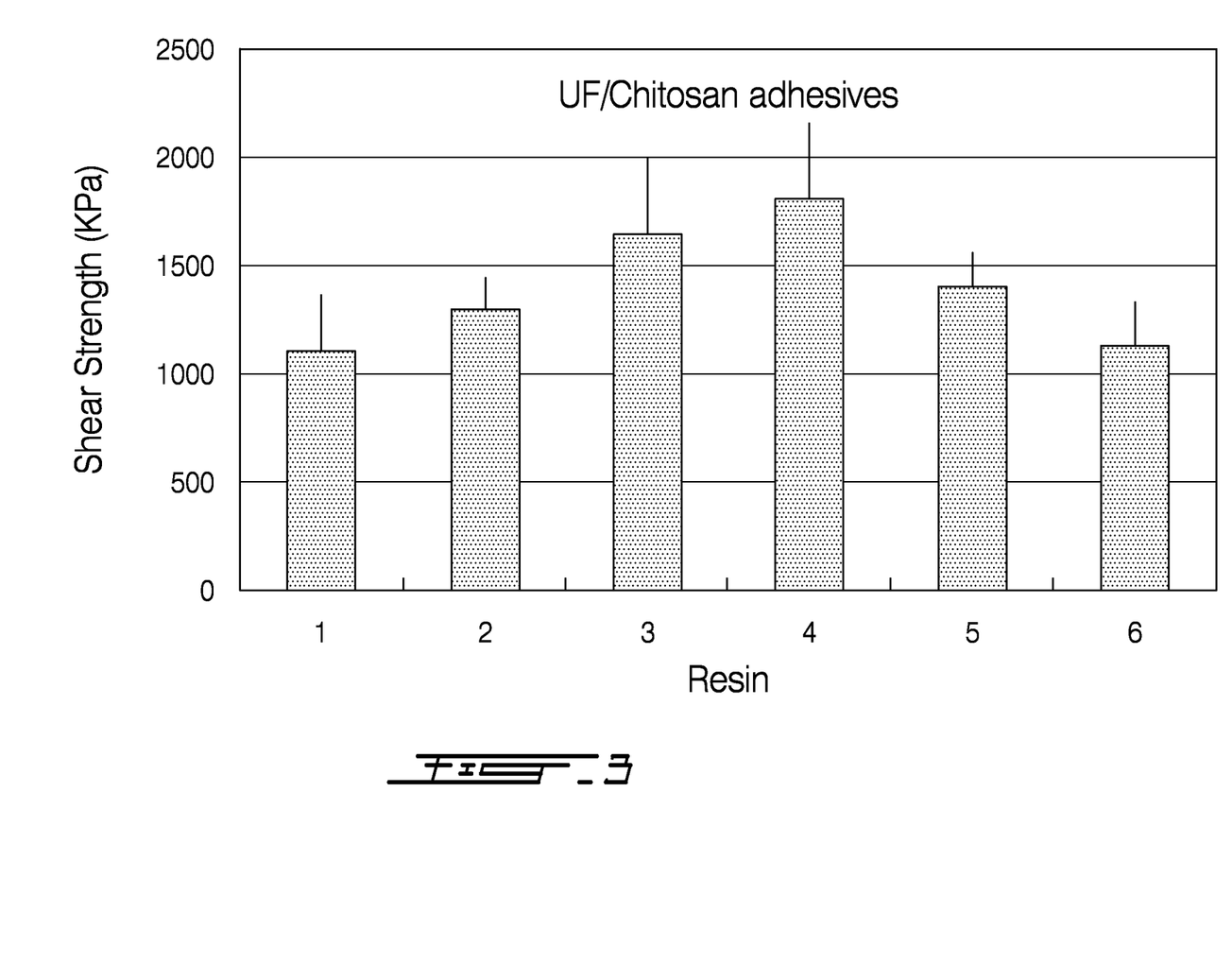
FIG. 3 is a histogram representing shear strengths of plywood samples comparing adhesives prepared with non-modified chitosan and adhesives using chitosan modified according to several embodiments of the present invention and reinforced with urea formaldehyde (UF) resin.

The lap-shear strengths of plywood samples made of enforced UF adhesives with fungal modified chitosan and unmodified chitosan are shown in FIG. 3. The abbreviations below the abscissa in FIG. 3 represent: 1=adhesive made of unmodified chitosan; 2=UF adhesive enforced with unmodified chitosan; 3=UF adhesive enforced with modified chitosan by fungal species *Gliocladium roseum* (FTK 321U); 4=UF adhesive enforced with modified chitosan by fungal species *Trichoderma viride* (FTK161D); 5=UF adhesive enforced with modified chitosan by fungal species *Trichoderma harzianum* (FTK160D); 6=commercial UF adhesive. Data presented in FIG. 3, are averages of 16 replicate specimens per treatment.

The plywood samples made of a commercial UF adhesive had lap-shear strength of 1129 kPa, which was similar to panels made of unmodified chitosan adhesive. Unmodified chitosan increased the bonding strength of UF adhesive to 1298 kPa. The shear strengths of samples made of enforced UF adhesives with fungal modified chitosan were highly increased; i.e. that enforced by modified chitosan by *Gliocladium roseum* (FTK 321U) was 1655 kPa, that enforced by modified chitosan by *Trichoderma viride* (FTK161D) was 1818 kPa, and that enforced by modified chitosan by *Trichoderma harzianum* (FTK160D) was 1407 kPa. In this set of test, plywood samples made of enforced UF adhesives with modified chitosan by *Trichoderma viride* (FTK161D) had the superior bonding properties to other adhesives.

Figure 4:
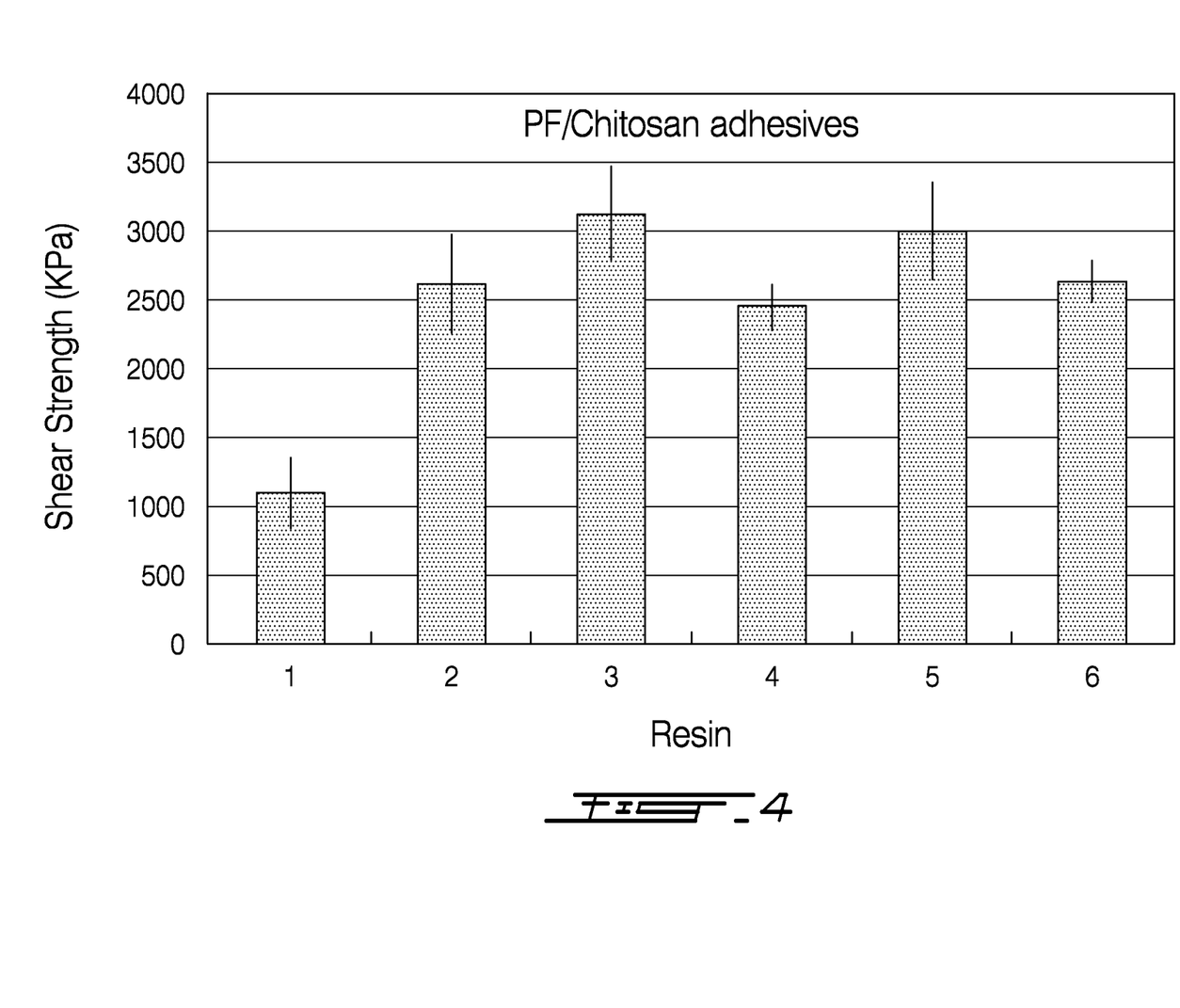
FIG. 4 is a histogram representing shear strengths of plywood samples comparing adhesives prepared with non-modified chitosan and adhesives using chitosan modified according to several embodiments of the present invention and reinforced with phenol formaldehyde (PF) resin.

The lap-shear strengths of plywood samples made of enforced PF adhesives with fungal modified chitosan and unmodified chitosan are shown in FIG. 4. The abbreviations below the abscissa of FIG. 4 represent: 1=adhesive made of unmodified chitosan; 2=PF adhesive enforced with unmodified chitosan; 3=PF adhesive enforced with modified chitosan by fungal species *Gliocladium roseum* (FTK 321U); 4=PF adhesive enforced with modified chitosan by fungal species *Trichoderma viride* (FTK161D); 5=PF adhesive enforced with modified chitosan by fungal species *Trichoderma harzianum* (FTK160D); and 6=PF commercial adhesive. The data in FIG. 4 derives from the average of 16 replicate specimens per treatment.

The plywood samples made of a commercial PF adhesive had lap-shear strength of 2633 kPa, which was higher than that of panels made of unmodified chitosan adhesive. Unmodified chitosan and chitosan modified by *Trichoderma viride* (FTK161D) did not increase the bonding strength of PF adhesive. The shear strengths of plywood samples made of the PF adhesive enforced with modified chitosan by *Gliocladium roseum* (FTK 321U) was 3128 kPa, and that enforced with modified chitosan by *Trichoderma harzianum* (FTK160D) was 2998 kPa. In this set of tests, plywood samples made of enforced PF adhesives with modified chitosan by *Gliocladium roseum* (FTK 321U) had the superior bonding properties to other adhesives. It should therefore be noted that the lap shear test results for phenolic resins with fungal modified chitosan are all greater than those obtained by Peshkova et al.

The embodiments of the invention described above are intended to be exemplary. Those skilled in the art will therefore appreciate that the foregoing description is illustrative only, and that various alternate configurations and modifications can be devised without departing from the spirit of the present invention. Accordingly, the present invention is intended to embrace all such alternate configurations, modifications and variances which fall within the scope of the appended claims.

The invention claimed is:

1. A fungal modified chitosan adhesive for a fibrous material produced by
   providing a chitosan containing raw material (2);
   providing a fungal growing medium (4);
   providing a fungal culture (6); wherein the fungal culture is at least one of species Ascomycota mitosporic fungi;
   mixing (10) the raw material (2), the growing medium (4) and the fungal culture together to produce a suspension (12);
   incubating (20) the suspension (12) to produce a broth (22) comprising a modified chitosan solid (32), an at least partially-consumed medium liquid (34) and a fungal residue (36);
   separating (30) the modified chitosan solid (32) from the liquid (34) and the fungal residue (36), and
   dissolving (40) the modified chitosan solid (32) to produce the adhesive resin (42).

2. The adhesive of claim 1, wherein dissolving the modified chitosan is in an acid.

3. The adhesive of claim 1, wherein dissolving the modified chitosan is in at least one of a urea formaldehyde resin or a phenol formaldehyde resin.

4. The adhesive of claim 1, wherein the fungal culture comprises at least one of *Trichoderma harzianum* Rifai, *Trichoderma viride* Pers.:Fr., and *Gliocladium roseum* Bainier.

5. The adhesive of claim 4, wherein providing the fungal culture is in a form of a Mycelia plug cultured on 2% malt extract agar medium at 25° C. for one week.

6. The adhesive of claim 1, wherein the medium (4) is produced of a sterile aqueous solution comprising at least one of $KNO_3$, $KH_2PO_4$, $MgSO_4.7H_2O$, $FeCl_3.6H_2O$, polyvinylpyrrolidone, and a nutrient solution containing at least one of a mineral and a vitamin for fungal growth.

7. The adhesive of claim 2, wherein the dissolving (40) is combined with:
  an in situ polymerization of a phenolic resin with the modified chitosan (32), or
  an in situ polymerization of a urea formaldehyde (UF) resin with the modified chitosan (32).

8. The adhesive of claim 1, wherein incubating the suspension (22) is for 21 days at 25° C.

9. The adhesive of claim 1, wherein separating (30) the broth (22) comprises
  filtering the broth (22) to remove the fungal residue (36) to produce a second broth comprising the modified chitosan solid (32) in the liquid (34), and
  filtering the second broth to remove the liquid (34) to produce the modified chitosan solid (32).

10. The adhesive of claim 9, wherein the separating (30) further comprises
  washing the modified chitosan solid (32) with water;
  drying the modified chitosan solid, and
  blending the modified chitosan solid into a fine chitosan powder.

11. A method of producing an adhesive resin (42) for fibrous products comprising:
  providing a chitosan containing raw material (2);
  providing a fungal growing medium (4);
  providing a fungal culture (6); wherein the fungal culture is at least one of sgecies Ascomycota mitosporic fungi;
  mixing (10) the raw material (2), the growing medium (4) and the fungal culture together to produce a suspension (12);
  incubating (20) the suspension (12) to produce a broth (22) comprising a modified chitosan solid (32), an at least partially-consumed medium liquid (34) and a fungal residue (36);
  separating (30) the modified chitosan solid (32) from the liquid (34) and the fungal residue (36), and
  dissolving (40) the modified chitosan solid (32) to produce the adhesive resin (42).

12. The method of claim 11, wherein dissolving (40) the modified chitosan solid is in an acid.

13. The method of claim 11, wherein dissolving (40) the modified chitosan solid is in at least one of a urea formaldehyde resin or a phenol formaldehyde resin.

14. The method of claim 11, wherein the fungal culture comprises at least one of *Trichoderma harzianum* Rifai, *Trichoderma viride* Pers.:Fr., and *Gliocladium roseum* Bainier.

15. The method of claim 14, wherein providing the fungal culture (6) is in a form of at least one Mycelia plug cultured on 2% malt extract agar medium at 25° C. for one week.

16. The method of claim 11, wherein the medium (4) is produced of a sterile aqueous solution comprising at least one of $KNO_3$, $KH_2PO_4$, $MgSO_4.7H_2O$, $FeCl_3.6H_2O$, polyvinylpyrrolidone, and a nutrient solution containing at least one of a mineral and a vitamin for fungal growth.

17. The method of claim 12, wherein the dissolving (40) is combined with:
  an in situ polymerization of a phenolic resin with the modified chitosan (32), or an in situ polymerization of a urea formaldehyde (UF) resin with the modified chitosan.

18. The method of claim 11, wherein incubating the suspension (12) is for 21 days at 25° C.

19. The method of claim 11, wherein separating (30) the broth (22) comprises
  filtering the broth (22) to remove the fungal residue (36) to produce a second broth comprising the modified chitosan solid (32) in the liquid (34), and
  filtering the second broth to remove the liquid (34) to produce the modified chitosan solid (32).

20. The method of claim 19, the separating (30) further comprises
  washing the modified chitosan solid with water;
  drying the modified chitosan solid, and
  blending the modified chitosan solid into a fine chitosan powder.

* * * * *